United States Patent
Wan et al.

(10) Patent No.: US 9,186,436 B2
(45) Date of Patent: Nov. 17, 2015

(54) POLY(VINYL ALCOHOL)-BACTERIAL CELLULOSE NANOCOMPOSITE

(75) Inventors: Wan-Kei Wan, London (CA); Leonardo Millon, London (CA)

(73) Assignee: AXCELON BIOPOLYMERS CORPORATION, London (CA)

( * ) Notice: Subject to any disclaimer, the term of this patent is extended or adjusted under 35 U.S.C. 154(b) by 967 days.

(21) Appl. No.: 12/216,809

(22) Filed: Jul. 10, 2008

(65) Prior Publication Data
US 2009/0028927 A1    Jan. 29, 2009

Related U.S. Application Data

(63) Continuation of application No. 10/639,683, filed on Aug. 13, 2003, now abandoned.

(51) Int. Cl.
| | |
|---|---|
| *C12P 19/04* | (2006.01) |
| *C08L 29/04* | (2006.01) |
| *C08L 1/02* | (2006.01) |
| *A61L 31/10* | (2006.01) |
| *A61L 27/48* | (2006.01) |
| *A61L 15/22* | (2006.01) |
| *A61L 31/12* | (2006.01) |

(52) U.S. Cl.
CPC .............. *A61L 27/48* (2013.01); *A61L 15/225* (2013.01); *A61L 31/10* (2013.01); *A61L 31/129* (2013.01); *C08L 29/04* (2013.01); *C12P 19/04* (2013.01); *A61L 2420/06* (2013.01); *C08L 1/02* (2013.01)

(58) Field of Classification Search
CPC ........... C12P 19/04; C08L 29/04; C08L 1/02; A61L 31/10; A61L 27/48
See application file for complete search history.

(56) References Cited

U.S. PATENT DOCUMENTS

| | | | |
|---|---|---|---|
| 4,524,064 A * | 6/1985 | Nambu | 424/445 |
| 4,575,551 A | 3/1986 | Fujiyama et al. | |
| 4,588,400 A * | 5/1986 | Ring et al. | 604/304 |
| 4,663,358 A | 5/1987 | Hyon et al. | |
| 4,742,164 A * | 5/1988 | Iguchi et al. | 536/56 |
| 5,558,861 A * | 9/1996 | Yamanaka et al. | 424/93.7 |
| 5,846,213 A * | 12/1998 | Wan | 602/49 |
| 5,958,420 A * | 9/1999 | Jenson | 424/771 |
| 6,231,605 B1 * | 5/2001 | Ku | 623/11.11 |
| 6,458,156 B1 | 10/2002 | Wan et al. | |
| 8,940,337 B2 * | 1/2015 | Li et al. | 424/501 |
| 2001/0044138 A1 | 11/2001 | Watanabe et al. | |
| 2004/0096509 A1 | 5/2004 | Hutchens et al. | |

FOREIGN PATENT DOCUMENTS

| | | |
|---|---|---|
| WO | 96/11721 | 4/1996 |
| WO | 01/30145 | 5/2001 |

OTHER PUBLICATIONS

Wan et al., "Optimizing the Tensile Properties of Polyvinyl Alcohol Hydrogel for the Construction of a Bioprosthetic Heart Valve Stent", Journal of Biomedical Materials Research (Applied Biomaterials) 2002, 63, pp. 854-861.

* cited by examiner

Primary Examiner — Cherie M Stanfield

(57) ABSTRACT

Hydrogel-bacterial cellulose nano-composite materials are created using a hydrogel and never dried bacterial cellulose fibers. Such materials are suitable for a broad range of soft tissue replacement applications. In addition controlled release of bioactive agents properties can be designed into medical devices fabricated from such composite materials.

19 Claims, 5 Drawing Sheets

POLY(VINYL ALCOHOL)-BACTERIAL CELLULOSE NANOCOMPOSITE

FIELD OF THE INVENTION

This invention relates to composite materials formed from a hydrogel and cellulose, and more particularly the present invention relates to new types of poly(vinyl alcohol)-bacterially produced cellulose composites suitable for soft tissue replacement and controlled release.

BACKGROUND OF THE INVENTION

Cardiovascular disease remains the leading cause of death in the United States, accounting for nearly 1 million deaths in 1996. Of these fatalities, 50% are attributed to coronary artery disease that arises from low-density lipoprotein (LDL) cholesterol, which transport about 75% of the cholesterol. It can penetrate the artery wall where it interacts with free radicals that attack and modify its form. The resulting oxidized form of LDL triggers white blood cells in the immune system to gather at the site, forming thick substance called plaque and causing inflammation. The plaque will build up eventually constricting the walls, in the process known as atherosclerosis [1].

The second most common heart operation in the western world is heart valve replacement [2]. The main types of replacement valves for heart valve replacements are mechanical and bioprosthetic, both with advantages and disadvantages. Mechanical heart valves are made of non-biologic materials, and their advantages are their durability and structural reliability. Their main disadvantages are the patient risk of thromboembolism due to the poor blood compatibility and flow abnormalities. To reduce the risk, the patient requires lifetime anticoagulant therapy [3, 4]. Bioprosthetic heart valves are made in part of animal tissue, thus maintaining a low level of thromboembolism without the need of long-term anticoagulant therapy. They also have improved hemodynamics because their flow pattern is similar to natural valves. However, their major disadvantage is their limited durability, due to structural dysfunction from calcification and noncalcific tissue deterioration. More than 50% of them fail between 10 to 15 years and require re-operation [3, 4, 5].

One of the most common treatments for coronary artery disease is coronary artery bypass surgery, which is the revascularization of the damaged myocardium [6]. Normally, a suitable length of the patient's saphenous vein is used to provide blood to the heart tissue. The main disadvantage is "vein graft disease", which is the deterioration and occlusion of the vein graft due to further advancement of the patient's coronary artery disease [7, 1].

Therefore, here lies the need to develop a material that will not only display similar mechanical properties as the tissue it is replacing, but also shows improved life span. One promising class of materials are hydrogels.

Hydrogels

Hydrogels are hydrophilic polymer networks produced from reactions of one or more monomers or by association bonds between chains that can absorb from at least 20% to up to thousands of times their dry weight in water [8, 9]. Hydrogels may be chemically stable or they may disintegrate and dissolve with time. They are called either physical (reversible) or chemical (permanent) hydrogels. Physical hydrogels have networks held together by molecular entanglements and/or secondary forces such as hydrogen bonding, van der Waals interactions, ionic or hydrophobic forces. Physical hydrogels are not homogeneous due to regions of high crosslinking density and low water swelling, called clusters, dispersed within low crosslinking density and high water swelling, or hydrophobic or ionic domains that create inhomogeneities. Chemical hydrogels are covalently crosslinked networks, but they may also be generated by crosslinking of water-soluble polymers, or by converting hydrophobic polymers to hydrophilic polymers. Chemical hydrogels are also not homogeneous due to clusters of molecular entanglements. Chain loops and free chain ends also produce network defects in both physical and chemical hydrogels, and they do not contribute to the permanent network elasticity [8, 10].

An important characteristic of hydrogels is their swelling behaviour in water, since after preparation they have to be in contact with water to yield the final solvated network structure. Highly swollen hydrogels are those of poly(vinyl alcohol) (PVA), poly(ethylene glycol), and poly(N-vinyl 2-pyrrolidone), among others. Poly(vinyl alcohol) (PVA) is a hydrophilic polymer with various characteristics desired for biomedical applications, such as high degree of swelling, uncomplicated chemical structure, rubbery/elastic nature, and non-toxic. PVA can be converted into a solid hydrogel by crosslinking. Crosslinking can be accomplished by using several methods. For biomedical applications, physical crosslinking has the advantages of not leaving residual amounts of the toxic crosslinking agent, and higher mechanical strength than the PVA gels crosslinked by either chemical or irradiative techniques. The mechanical properties of the PVA hydrogels are similar to that of soft tissue, including elasticity and strength, and can be controlled by changing the number of thermal cycles, PVA concentration, thawing rate of the thermal cycling process, and freezing holding time among other parameters [11, 12, 13]. A PVA based bioprosthetic heart valve stent has been fabricated. However, the mechanical strength and stiffness of these PVA materials were weak and did not fully match the mechanical properties displayed by the cardiovascular tissues such as arteries and heart valves.

Poorly swollen hydrogels are those of poly(hydroxyethyl methacrylate) (PHEMA) and its derivatives. However, the desired swelling properties can be achieved by copolymerization of a hydrophilic monomer with a less hydrophilic one. This gives a vast range of swellable hydrogels, and the swelling characteristics are of great importance for biomedical and pharmaceutical applications. This equilibrium degree of swelling affects the solute diffusion coefficient through these gels (control release applications), the surface properties and mobility (coating applications), the optical properties (contact lenses applications), and the mechanical properties of the hydrogel (tissue replacement applications) [14].

The main areas in which hydrogels are used as biomaterials is in contact lenses, synthetic wound coverings, drug delivery systems, organ and tissue replacements, and permselective membranes [8, 14, 10, 15, 16, 11, 17, 18, 19, 5, 20, 13]. One of the major disadvantages of hydrogels is that when dehydrated, they are hard and brittle, but when swollen in water, they become rubbery with a very low tear and tensile strength. This has a profound effect on the life span of the lenses. Most of the research tries to improve the mechanical properties by looking at a variety of polymer combinations and cross-linking agents, such as acrylamide and acrylonitrile-based hydrogels, and vinyl pyrrolidone copolymers [21].

PVA has a relatively simple chemical formula with a pendant hydroxyl group and a crystalline nature, which allows it to form a solid hydrogel by the crosslinking of the PVA polymer chains. Vinyl alcohol (monomer) does not exist in a stable form and rearranges to its tautomer, acetaldehyde. PVA is produced by free radical polymerization of vinyl acetate to poly(vinyl acetate) (PVAc), and subsequent hydrolysis of PVAc gives PVA [12].

PVA can be crosslinked using several methods, such as the use of crosslinking chemical agents, using an electron beam or γ-irradiation, or the physical crosslinking due to crystallite formation. For biomedical applications, physical crosslinking has the advantages of not leaving residual amounts of the toxic crosslinking agent, and higher mechanical strength than the PVA gels crosslinked by either chemical or irradiative techniques [22, 23]. In chemical cross-linking, the chemical agents that react with the hydroxyl groups are glutaraldehyde, ethylaldehyde, terephthalaldehyde, formaldehyde, hydrochloric, boric or maleic acid, among others [11, 24]. Physical crosslinking forms a hydrogel with a network of semi-crystallites of hydrogen bonds of polymer filled with solvent [25]. It has been shown that the mechanical properties of the hydrogels, including elasticity and strength, can be altered by changing the PVA concentration, the number of freeze/thaw cycles, the process thawing rate, the freezing holding time, and the freezing temperature [11, 26, 27]. Increasing the PVA concentration results in hydrogels with higher crystallinity and added stability upon swelling, which increases its tensile strength and tear resistance. The lower the initial concentration of PVA, the fewer the polymer chains in solution, and there may be less number of crystalline regions created in the cycled PVA. Increasing the number of freeze/thaw cycles increases the strength and stiffness of the hydrogel by reinforcing existing crystals within the structure [11, 28, 13]. Decreasing the thawing rate of frozen PVA solutions increases the tensile strength because the solutions are kept for longer periods at temperatures below 0° C., allowing for increasing movements of polymer chains which result in further entanglements and increased crystallite size and numbers. The freezing holding time also has a drastic effect, with samples frozen up to 10 days giving the most mechanically strong PVA hydrogels [24, 13, 25, 27]. The freezing temperature has an interesting effect. The freezing temperature controls the phase equilibria and dynamics, where the lower the temperature of the system the lower the amount of unfrozen solvent in the liquid regions. Therefore, the lower the temperature the less opportunity for chain mobility in the polymer rich regions, giving less chances of crystallite growth and formation. This explains why keeping the frozen PVA solutions at −10° C. produces somewhat more rigid hydrogels than those kept for the same period of time at −20 or −30° C. The freezing rate was shown not to have drastic effects on the properties of the hydrogel [11, 13, 25]. PVA hydrogels not only have tensile strength and elongation, but also flexibility and elasticity. Research has proven its ability to recover to its original shape after being deformed to strains of 50%, showing excellent persistence and repeatability of the recovery [25].

Physical crosslinking allows the PVA hydrogels to retain their original shape and be extended up to six times their size. This behaviour shows its rubbery and elastic nature and the high mechanical strength [29, 26]. There are various theories proposed in the literature to explain why thermal cycling increases the elastic modulus of PVA. The most accepted theory describes the physical cross-linking process as an entropic reordering phenomena. Water is likely to bind to the polymer by hydrogen bonding. When the solution freezes, ice crystals force the polymer chains close to each other forming high local polymer concentration regions or nuclei. When the material thaws, these nuclei act as crosslinking sites for polymers molecules, which realign and form hydrogen bonds to form crystallites and polymer chain entanglements. The crystalline regions are formed within the polymer rich regions, with further cycling increasing both the size and number of the crystalline regions by repeating the process [11, 30, 29]. On a molecular level, the crystallites of PVA can be described as layered structure, with a double layer of molecules held together by hydroxyl bonds, while weaker van der Waals forces-operate between the double layers. This folded chain structure leads to ordered regions (crystallites) within an unordered, amorphous polymer matrix [12]. The mechanical properties of PVA are very unique compared to other polymers. The stress-strain curves for the polymeric materials are initially linear and then curve towards the strain axis. On the other hand, the PVA curve displays an exponential stress-strain curve similar to the characteristics of soft biological tissues, with the curve shifting towards the stress axis.

PVA materials have been reported to be ideal candidates as biomaterials, due to their high degree of swelling, uncomplicated chemical structure, rubbery/elastic nature, non-toxic, non-carcinogenic, and bioadhesive characteristics. Some of the biomedical applications include tissue reconstruction and replacements, cell entrapment and drug delivery, soft contact lens material, wound covering bandage for burn victims, quality control phantom for MR, among other medical applications [30, 12].

Although PVA hydrogel can be processed to possess mechanical properties similar to some soft biological tissues, there are tissues such as heart valve cusps and cartilage that have mechanical properties that are beyond the range of the low temperature processed PVA. Also, for medical device applications, for durability, the most ideal material would be one that has mechanical properties that mimic the soft tissue to be replaced within the physiological range but stronger beyond this range. These requirements imply that a material more than PVA is required for good, durable medical device applications. One approach is to create a PVA based composite that possesses the properties requirements outlined.

Therefore there is a need for a composite material that has properties similar to that of natural tissue for medical device applications. Moreover, if would be a further advantage if such material is capable of delivering bioactive agent locally where the device is implanted.

Bacterial Cellulose

Bacterial cellulose has many characteristics that make it valuable for biomedical applications, including its polyfunctionality, hydrophilicity, and biocompatibility [33]. Cellulose is a linear polymer made of glucose molecules linked by β(1-4) glycosidic linkages. Its chemical formula is $(C_6H_{10}O_5)_n$. There are four principle sources of cellulose. The majority of cellulose is isolated from plants. A second source is the biosynthesis of cellulose by different microorganisms, including bacteria (*acetobacter, aerobacter, pseudomonas*), algae, and fungi among others. The other two less common sources include the enzymatic in vitro synthesis starting from cellobiosyl fluoride, and the chemosynthesis from glucose by ring-opening polymerization of benzylated and pivaloylated derivatives [31, 32]. Cellulose is not uniformly crystalline, but ordered regions are extensively distributed throughout the material, and these regions are called crystallites. The long cellulose chains lie side by side held together by hydrogen bonds between the hydroxyl groups. These chains are twisted into structures called microfibrils, which are twisted into fibers [33, 31].

Bacterial cellulose is produced by strains of the bacterium *Acetobacter xylinum*, which is typically found on decaying fruits, vegetables, vinegar, fruit juices, and alcoholic beverages. It is a Gram-negative, rod shaped and strictly aerobic bacterium. Bacterial cellulose produced has very high purity and contains no lignin, hemicelluloses, pectin, and waxes as plant cellulose does. Therefore, production of bacterial cellulose has the advantage of not requiring the harsh chemical treatment needed for plant cellulose production. This chemical treatment also has the disadvantage of altering the natural structural characteristics of cellulose [33, 31, 32]. Bacterial cellulose differs from plant cellulose with respect to its high crystallinity, ultra-fine network structure, high water absorption capacity, high mechanical strength in the wet state, and availability in an initial wet state [32]. Bacterial cellulose pellicles are formed in static culture. The pellicle has an ultra-fine network structure of ribbons 500 nm wide and 10 nm thick. The ribbons consisted of smaller microfibrils with a width of around 3 nm and a fiber diameter of less than 130 nm compared to the over 14 mm found in birch [31, 32]. Bacterial cellulose including the pellicle possesses a high water retention capacity. Water retention values can reach up to 1000%, which are significantly higher than that for plant cellulose. The water retention is drastically decreased after air-drying the bacterial cellulose and reswelling in water, with values comparable to those of plant cellulose [31, 32].

Bacterial cellulose can also be prepared in shake culture in flasks and in agitated culture in a bioreactor. These approaches are more efficient methods for bacterial cellulose production and are preferred for large scale production of bacterial cellulose.

Bacterial cellulose, being a hydrophilic, highly water swollen and biocompatible natural polymer which is ideally suited to be the reinforcing fibers in the preparation of a composite material for soft tissue replacement devices. Such composite material can be created when it is used in combination with PVA.

Fiber reinforced composites provide improved strength, stiffness, and fatigue resistance. The softer, more elastic matrix transmits the force to the fibers, which normally carry most of the applied force. The modulus of elasticity and strength of the composite depend on various factors. The fibers can be short, long, or continuous with typical diameters in the range of 10 to 150 microns. The larger the aspect ratio (length/diameter) of the fibers, the higher the strength of the composite. The greater the fiber volume fraction also increases the composite strength and stiffness up to 80%. The orientation of the fibers is also an important factor. Short, randomly orientated fibers give relatively isotropic behaviour. Long, unidirectional arrangements of fibers produce anisotropic properties, with good strength and stiffness in the orientation parallel to the fibers. The raw fiber properties are important, with strong, stiff, and lightweight fibers being the most commonly used. The matrix properties are also important, supporting the fibers, keeping them in the proper position, transferring the load to the fibers, and preventing cracks in the fibers. Therefore, good bonding between the fibers and the matrix is required for the successful transfer of load in the composite [34]. Joining two or more materials may give composites with properties not attainable by the original materials. The materials are selected to improve properties such as stiffness, strength, corrosion resistance, high-temperature performance, and conductivity [34].

Uryu [35] reported the formation of a biodegradable polymeric material that can be decomposed in soil. The bacterial cellulose (with ribbon shaped micro-fibrils) that can be biologically decomposed by microbes was mixed with a biodegradable polymeric material to produce an improved composite with higher tensile strength. The bacterial cellulose was produced in a liquid culture medium using different types of microbes, including *Acetobacter xylinum*, collected and dried into a powdery state and mixed with the polymer to produce the composite. Various polymers were used, including PVA. The composites ranged from bacterial cellulose concentrations as low as 1% to 99%. The final composite was dried and used for high-strength cabinets for audio/video apparatus. After the lifetime of the device is reached, the composite material can be buried in the ground for waste disposal and it is eventually decomposed to protect the environment.

SUMMARY OF THE INVENTION

An objective of this invention is to provide new types of PVA-bacterial cellulose composites suitable for soft tissue replacement and controlled release. These new materials would be useful in the design and fabrication of medical devices.

In one aspect of the invention there is provided a hydrogel/cellulose composite material including a hydrogel present in an amount from about 5% by weight to about 20% by weight, cellulose present in a range from about 0.05% by weight to about 5% by weight and a remainder being a solvent, the cellulose including fibers having nanometer scale cross sectional dimensions.

The present invention provides a hydrogel/cellulose composite material, comprising a hydrogel including polyvinyl alcohol (PVA) present in an amount from about 5% by weight to about 20% by weight, cellulose present in a range from about 0.05% by weight to about 5% by weight and a remainder being water, the cellulose including fibers having nanometer scale cross sectional dimensions produced using a microbial fermentation process using a bacterium *Acetobacter xylinum*.

In another aspect of the invention there is provided a process of producing a composite material comprising a hydrogel and cellulose, comprising the steps of synthesizing cellulose using an effective bacteria in a microbial fermentation synthesis process to give a suspension of cellulose fibers having nanometer scale cross sectional dimensions, isolating the cellulose fibers produced by the microbial fermentation process and forming an aqueous cellulose suspension of the cellulose fibers while preventing the cellulose fibers from being dried out between the time they are produced and suspended in an aqueous liquid. A mixture is formed by mixing a hydrogel material with the aqueous cellulose suspension, and heating the resulting mixture at a sufficiently high temperature for a sufficiently long period of time for the hydrogel material to dissolve into solution, thereafter solidifying the mixture to form the composite material.

In another aspect of the invention there is provided a process of producing a composite material comprising a hydrogel and cellulose, comprising the steps of synthesizing cellulose using an effective bacteria in a microbial fermentation synthesis process to give a suspension of cellulose fibers having nanometer scale cross sectional dimensions, isolating the cellulose fibers produced by the microbial fermentation process and forming an aqueous cellulose suspension of the cellulose fibers while preventing the cellulose fibers from being dried out between the time they are produced and suspended in an aqueous liquid. A mixture is formed by mixing a hydrogel material with the aqueous cellulose suspension, and heating the resulting mixture at a sufficiently high temperature and for a sufficiently long period of time for the hydrogel material to dissolve into solution, thereafter solidifying the mixture to form the composite material. The composite material is then thermally cycled selected temperatures an effective number of times at selected cooling and heating rates to give the composite material pre-selected tensile properties.

The present invention also provides a composite material comprising a hydrogel and a cellulose with the composite material produced according to a method comprising the steps of synthesizing cellulose using an effective bacteria in a microbial fermentation synthesis process to give a suspension of cellulose fibers having nanometer scale cross sectional dimensions, isolating the cellulose fibers produced by the microbial fermentation process and forming an aqueous cellulose suspension of the cellulose fibers while preventing the cellulose fibers from being dried out between the time they are produced and suspended in an aqueous liquid. A mixture is then formed by mixing a hydrogel material with the aqueous cellulose suspension, and heating the resulting mixture at a sufficiently high temperature for a sufficiently long period of time for the hydrogel material to dissolve into solution, thereafter solidifying the mixture to form the composite material, the hydrogel being present in an amount from about 5% by weight to about 20% by weight and the cellulose present in a range from about 0.05% by weight to about 5% by weight, and a remainder being water.

In this aspect of the invention the hydrogel material is present in an amount from about 5% by weight to about 20% by weight, the cellulose is present in a range from about 0.05% by weight to about 5% by weight, and wherein a remainder of the composite material is water. The hydrogel material may be polyvinyl alcohol (PVA), and the bacteria may be *Acetobacter xylinum*.

BRIEF DESCRIPTION OF THE DRAWINGS

Preferred embodiments of the invention will now be described, by way of example only, with reference to the drawings, in which.

DETAILED DESCRIPTION OF THE INVENTION

Figure 1:
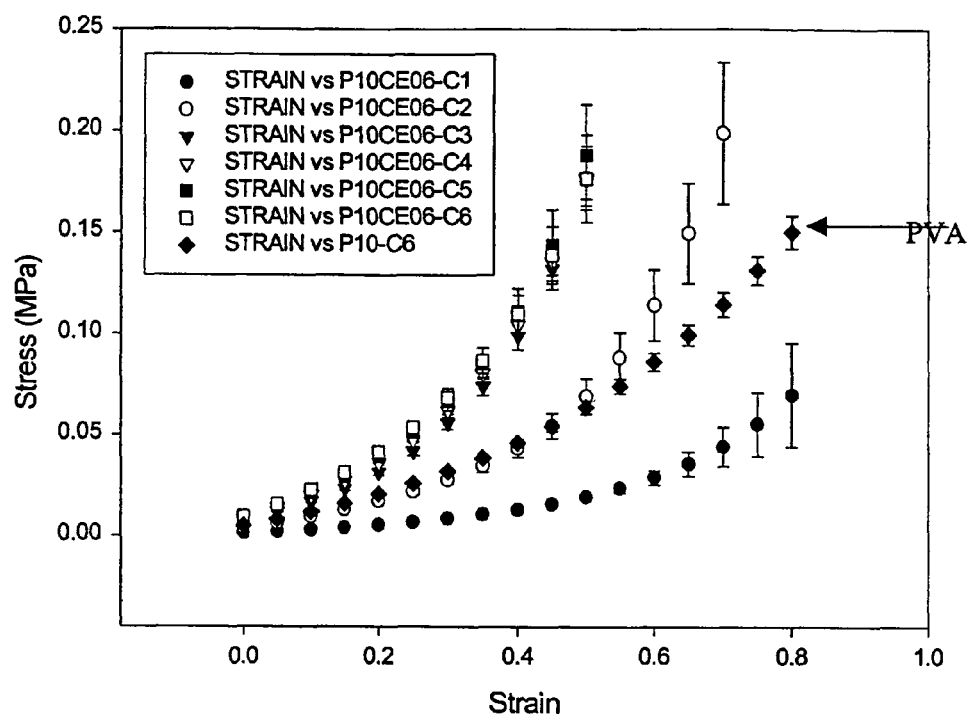
FIG. 1 shows stress-strain curves for 10% PVA samples containing 0.6% bacterial cellulose undergoing low temperature thermal cycling of cycles 1 through 6. The results are compared to that of 10% PVA cycle 6.

A composite material based on a combination of a hydrogel in combination with microbially-produced cellulose having cross sectional dimensions on the nanometer scale is disclosed herein along with a method of making the composite. The microbially-produced cellulose is produced in its original as produced state and is not dried but used directly to produce the composite. The microbially-produced cellulose may be produced from a bacterium. The genus of the bacterium may be *Acetobacter, Pseudomonas, Achromobacter, Alcaligene, Aerobacter* or *Azotobacter*. The microbially-produced cellulose may be produced from a fungus. The genus of the fungus may be *Chaetomium, Saccharomyces, Candida, Pichia* or *Fusarium*. The preferred microbially-produced cellulose is produced using a microbial fermentation process using the bacteria *Acetobactor xylinum* in either a static, shaken or agitated culture as disclosed in U.S. Pat. No. 5,846,213 (which is incorporated herein by reference).

The hydrogel can be chosen from the following list including polyvinyl alcohol (PVA), poly(vinyl pyrrolidone) (PVP), poly(ethylene glycol) (PEG), poly(hydroxyethyl methacrylate) (PHEMA) and polyacrylamide. Polyvinyl alcohol is the preferred choice for the purpose of this invention.

The hydrogel can be dissolved in a hydroxylic solvent including water, alcohol, ketone and aldehyde or carboxylic acid, or any other aprotic solvent capable of forming effective hydrogen bonding to dissolve PVA. Examples of dipolar aprotic solvents which may be used include dimtheyl sulfoxide (DMSO), dimethyl formamide (DMF), dimethyl acetamide (DMAc) and N-methyl pyrrolidone (NMP).

If the solvent is not water, the solvent would have to be removed by solvent exchange with water by immersion in water before use. As described above, the composite material can either be prepared using water as the solvent or solvent systems consisting of combinations of water and other solvents. The final product consists of microbial cellulose, hydrogel and the solvent used. In the case when either water is used in combination with other solvents or when solvent systems not containing water are used in the fabrication process, an additional step of solvent exchange with water will be necessary to replace the non-water solvent before the resulting product can be used for biomedical applications.

Bacterial cellulose is blended into the hydrogel solution and the composite material is solidified into the desired shape of the intended medical device. In the case of polyvinyl alcohol-bacterial cellulose nanocomposite, properties of the composite is a function of polyvinyl alcohol concentration, bacterial cellulose concentration and the processing conditions used to generate the composite material. The polyvinyl alcohol concentration may be in the range of 5 to 20 wt %, and the bacterial cellulose concentration in the range of 0.05 to 5 wt % may be used with the balance being the solvent system used in preparing the hydrogel solution.

The low temperature thermal cycling method is preferred in creating the PVA-bacterial cellulose composite material. In this case, material properties are a function of the number of thermal cycles, the freezing and thawing rate. Another method that can be used is fast cooling followed by cold soaking and controlled thawing.

The composite material produced according to the method disclosed herein may be formed into various pre-selected shapes for use as medical devices. Non-limiting examples include forming the composite material in the shape of a substantially planar sheet for a wound dressing, dental implant, vascular grafts, catheter covering dressing, dialysis membrane, coating for cardiovascular stents, coating for cranial stents, and membrane for tissue guided regeneration.

This invention is further illustrated by the following non-limiting examples.

EXAMPLES

PVA Solution Preparation

The PVA solution prepared was 5-15% by weight. This concentration was chosen as reference for the purpose of comparison against previous results and among different PVA composite materials. The procedure for PVA preparation was consistent with the protocol implemented by Wan [36]. The PVA used in all the experiments was purchased from Aldrich Chemical Company (Catalogue No. 36,306-5). A preferred PVA average molecular weight range (Mw) was 124,000 to about 186,000, 99+% hydrolysed and was received in powder form. The PVA solution in distilled water was prepared in a Pyrex resin flask combined with a reflux column to prevent excess vapor pressure build-up and water loss. The solution was heated between 2-3 hours at a temperature of around 80° C. When all the PVA had gone into a clear jelly-like solution, the flask was removed from the heating mantle.

More broadly, the polyvinyl alcohol (PVA) may have a molecular weight in a range from about 100,000 to about 200,000. If the molecular weight of PVA changes, in order to achieve the same mechanical properties, the corresponding cellulose concentration range will be adjusted accordingly.

Bacterial Cellulose Production

A 1.5 L stirred tank bioreactor equipped with a disk flat blade turbine and temperature and pH control was used for bacterial cellulose production. An incoulum was prepared using the bacteria *Acetobacter xylinum* (ATCC#700178). It was added to the sterile media and the mixture was allowed to mix at 28° C., pH of 5, air flow rate of 1 L/min and a mixing speed of 700 rpm for 72 hours. The media used has the following composition. Fructose 4% w/v, corn steep liquor 4% v/v, ammonium sulphate 0.33% w/v, potassium dihydrogen phosphate 0.1% w/v, magnesium sulphate heptahydrate 0.025% w/v, tri-sodium citrate 0.42% w/v and citric acid 0.88% w/v. After 72 hours, the reactor was shut down and its contents were centrifuged to remove the bacterial cellulose fibres from the spent broth. The crude bacterial cellulose was treated with 1 N sodium hydroxide at 90° C. for 30 minutes to remove any bacteria that still may be clinging to the fibres. The mixture was then centrifuged to recover the bacterial cellulose. The treated bacterial cellulose was washed three times with distilled water to remove any excess sodium hydroxide. The purified bacterial cellulose was stored in distilled, purified water in the refrigerator at around 6° C.

PVA-Bacterial Cellulose Solution Preparation

Two different methods of making up the PVA-cellulose solution may be used depending on the composition of PVA-cellulose solution. When preparing a low concentration cellulose and PVA solution, the preferred method is to start with the cellulose in suspension and add solid PVA to it, while when making up a higher concentration of cellulose and PVA solution, the preferred method is to mix PVA already in a solution with a cellulose suspension of known concentration. It will be understood that the difference between these two methods of making up the PVA-cellulose solution is more for convenience than being critical to the solution preparation procedure.

Suspensions of microbial cellulose nanofibres in distilled water in the range of 0.3-0.5 wt % are prepared. The suspension is added to PVA solution with mechanical stirring such that the final concentration of PVA is in the range of about 5 to about 15% and microbial cellulose concentration is between about 0.15 to about 0.5%. Depending on the viscosity of the resulting solution, extra care must be taken to prevent air bubble introduction in the mixer process. Table 1 contains a summary of the PVA-bacterial cellulose samples prepared.

As seen on Table 1, the concentrations were widely varied to observe the effects of both components on the material properties. First, a 10% PVA concentration was kept constant and the concentration of bacterial cellulose was varied from 0.15 to 0.61%, which was the highest concentration of cellulose obtained. Then, a ~0.31% bacterial cellulose concentration was kept constant, varying the PVA concentration from 7.5 to 15%. The two extremes were also investigated, a low PVA and low bacterial cellulose (5% PVA-0.15% bacterial cellulose), as well as a high PVA and high bacterial cellulose concentration (15% PVA-0.5% bacterial cellulose).

TABLE 1

| Solution | PVA Concentration (wt %) | Bacterial Cellulose Concentration (wt %) |
| --- | --- | --- |
| 1 | 5 | 0.15 |
| 2 | 7.5 | 0.32 |
| 3 | 10 | 0.15 |
| 4 | 10 | 0.23 |
| 5 | 10 | 0.31 |
| 6 | 10 | 0.61 |
| 7 | 12.5 | 0.32 |
| 8 | 15 | 0.31 |
| 9 | 15 | 0.5 |

PVA and PVA Composites Sample Preparation

After preparing PVA or the different PVA composites, the solution was poured or injected using large syringes onto stainless steel molds, with rubber spacers of either 1.6 or 3 mm thickness. These moulds were placed vertically into a temperature controlled bath. The freezing and thawing rate were kept constant at 0.1° C./min and the samples were cycled between about +20° C. to about −20° C. for 6 cycles.

Mechanical Testing

Tensile properties (stress-strain) and relaxation properties (stress remaining vs. time) of the PVA-bacterial cellulose composite were determined using a MTS tensile tester.

Material Properties

Mechanical properties for the PVA-bacterial cellulose composite were determined for the composition of 10% PVA and 0.61% bacterial cellulose and compared to that of PVA reference. FIG. 1 shows the stress-strain curves for samples undergoing low temperature thermal cycling of cycles 1 through 6. The curve for the 10% PVA reference (cycle 6) was also included for comparison purposes.

There are significant differences of the stress-strain relationship and the PVA-bacterial cellulose composite. Referring to FIG. 1, the stress-strain curve of the 10% PVA cycle 6 is similar to that of 10% PVA with 0.61% bacterial cellulose cycle 2 up to a strain of 45%. At this point, the stiffness of the material greatly increases and deviates from the curve of the PVA reference. This difference can be attributed to the presence of the bacterial cellulose in the composite.

Effect of Changing Bacterial Cellulose Concentration

Figure 2:
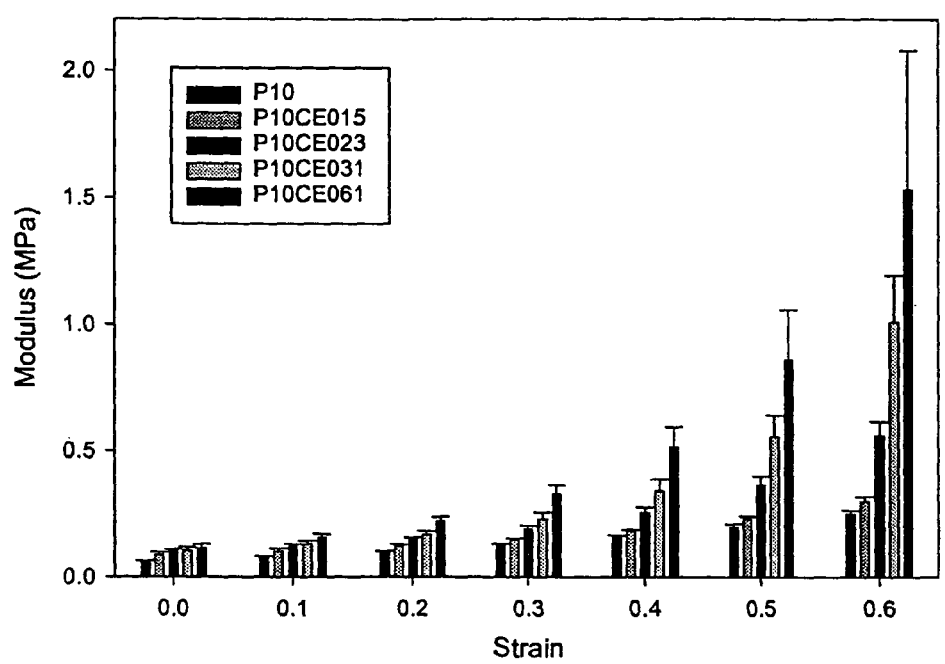
FIG. 2 shows modulus-strain plots showing the elastic moduli of 5 composites with 10% PVA andvarious bacterial cellulose concentrations (0, 0.15, 0.23, 0.31, 0.61%) for cycle 6.

The effect of the two components can be seen when comparing the moduli as a function of the strain while keeping one component constant. FIG. 2 shows the moduli of 5 composites with 10% PVA and various bacterial cellulose concentrations (0, 0.15, 0.23, 0.31, 0.61%) for cycle 6. It can be clearly seen the increase in modulus by adding extremely small amounts of bacterial cellulose, with an increase in modulus of almost 3 times at 30% strain and more than 6 times for 60% strain by adding 0.61% bacterial cellulose.

Scope of Mechanical Properties Control

In addition to 10% PVA, two extreme concentrations were also examined, including a low concentration of 5% PVA with 0.15% bacterial cellulose, and a high concentration of 15% PVA with 0.5% bacterial cellulose. These two compositions gave results that defined the limits of mechanical properties of the PVA-bacterial cellulose composites studied. FIG.

3 shows the stress-strain curves for cycle 6 of all the 9 PVA-bacterial cellulose composites, including these two extremes, and the reference 10% PVA. The moduli up to 40% strain for all the 9 composite compositions and the reference PVA can be seen on FIG. 4.

Figure 3:
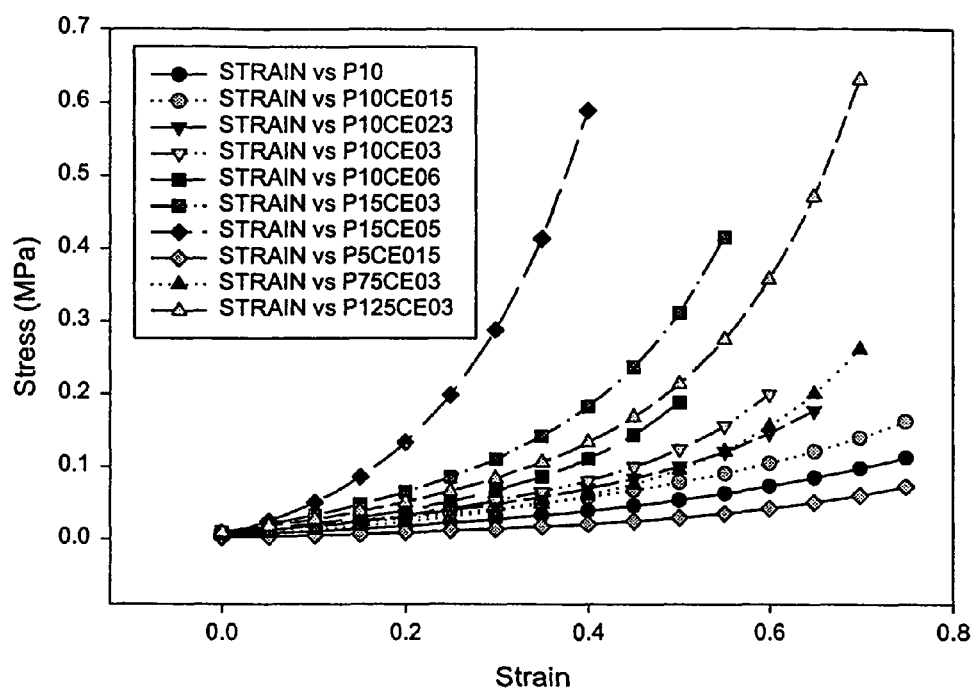
FIG. 3 shows stress-strain curves for cycle 6 of all the 9 PVA-bacterial cellulose composites (7.5-15% PVA, 0.15-0.6% bacterial cellulose), and the reference 10% PVA (P10)
Figure 4:
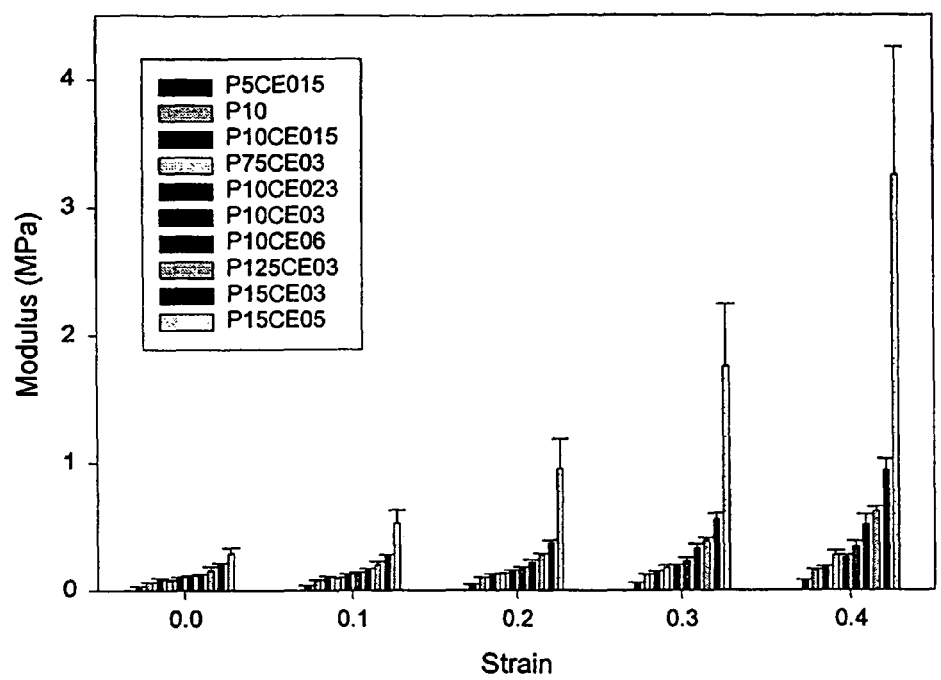
FIG. 4 shows a comparison of the moduli between 0-40% strain for the 9 PVA-bacterial cellulose composite and the reference 10% PVA (P10)

FIGS. 3 and 4 illustrates that any tissue with mechanical properties that fall between this range of stress-strain curves can be matched by a PVA-bacterial cellulose composite with an appropriate composition of components. The stress-strain curves presented in FIG. 3 are only for cycle 6. It is therefore clear that the range of mechanical property control is very broad. Thus, the stress-strain curve of any target tissue falling within this range can be matched by altering and controlling a combination of variables, including PVA and bacterial cellulose concentrations, number of freeze/thaw cycles, thawing rate, and freezing holding time, among other parameters. A large increase in modulus and stiffness was obtained by the high concentration composite (15% PVA with 0.5% bacterial cellulose) and for the first time a very stiff PVA material at low strains was obtained.

Figure 5:
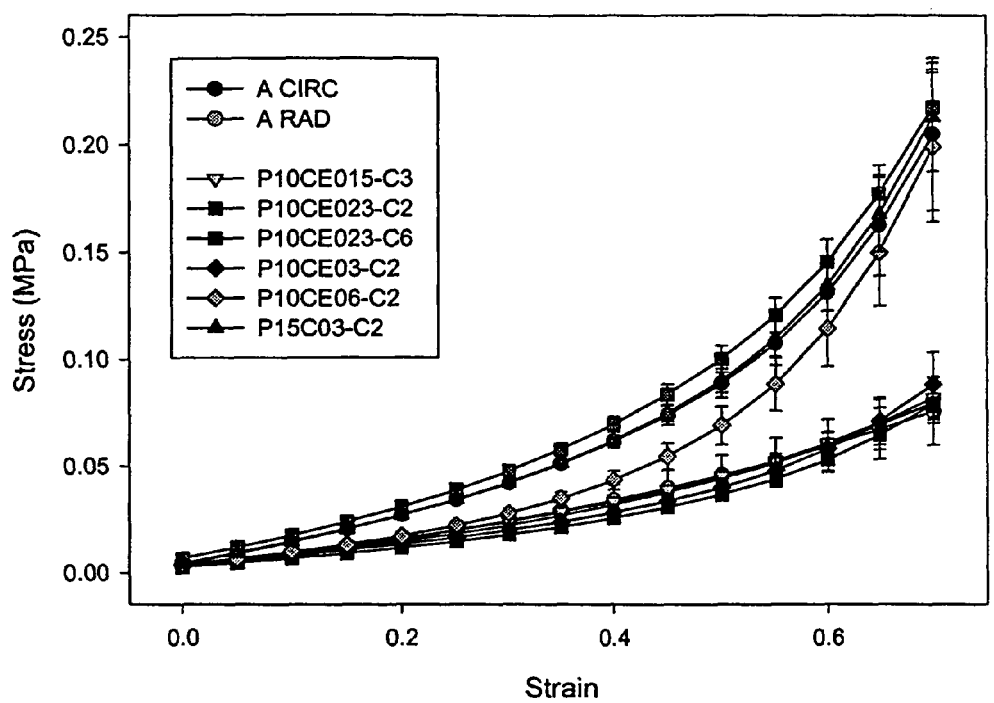
FIG. 5 shows a comparison of the stress-strain curves of various concentrations and cycles of PVA-bacterial cellulose composites (PVA 10-15%, bacterial cellulose 0.15-06%), PVA (10%) and porcine aortic root in the circumferential (A CIRC) and the radial (A RAD) directions.

Matching of PVA-Bacterial Cellulose Composite Properties to that of the Aortic Root The stress-strain curves for porcine aortic root in both directions were similar to the stress-strain curves of various types of PVA-bacterial cellulose composites. FIG. 5 shows the comparison of the stress-strain curves of various concentrations and cycles of PVA-bacterial cellulose composites and circumferential and radial aortic root. As seen in FIG. 5, there are various parameters that can be altered to obtain similar mechanical properties to the targeted aortic root tissue in any direction. The stress-strain curve of aortic root in the circumferential direction was similar to three different bacterial cellulose composites, including the 10% PVA with 0.61% bacterial cellulose cycled 2 times, the 15% PVA with 0.31% bacterial cellulose cycled 2 times, and the 10% PVA with 0.23% bacterial cellulose cycled 6 times. The stress-strain curve of aortic root in the radial direction was similar to four different bacterial cellulose composites, including the 10% PVA cycled 4 times, the 10% PVA with 0.31% bacterial cellulose cycled 2 times, the 10% PVA with 0.15% bacterial cellulose cycled 3 times, and the 10% PVA with 0.23% bacterial cellulose cycled 2 times.

PVA had been reported as an ideal cell entrapment material for cell immobilization carriers, due to their physico-chemical, thermal, mechanical, and biological stability and highly porous structure that facilitates the nonhindered diffusion of solutes and dissolved gases [13]. These characteristics are important for drug delivery applications. The bacterial cellulose-PVA composite with a cellulose concentration in the range of 0.05-0.5% is expected to retain all these useful characteristics of PVA.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Popma, J. J., et al. "Lipid-Lowering Therapy After Coronary Revascularization." *American Journal of Cardiology* 86.4B (2000): 18H-28H.
2. Korossis, S. A., J. Fisher, and E. Ingham. "Cardiac Valve Replacement: A Bioengineering Approach." *Bio-medical Materials and Engineering* 10.2 (2000): 83-124.
3. Schoen, F. J., and R. J. Levy. "Founder's Award, 25$^{th}$ Annual Meeting of the Society for Biomaterials, Perspectives. Providence, R.I., Apr. 28-May 2, 1999. Tissue Heart Valves: Current Challenges and Future Research Perspectives." *Journal of Biomedical Materials Research* 47.4 (1999): 439-65.
4. Vogt, P. R., and M. I. Turina. "Aortic Valve Replacement: Technique and Outcome with Artificial Heart Valves and Allografts." *Therapeutische Umschau* 55.12 (1998): 737-45.
5. Vyavahare, N. R., et al. "Current Progress in Anticalcification for Bioprosthetic and Polymeric Heart Valves." *Cardiovascular Pathology* 6.4 (1997): 219-229.
6. Linardakis, N. *Anatomy*. New York: McGraw-Hill, 2000.
7. Sinnatamby, C. S. *Last's Anatomy: Regional and Applied*. 10$^{th}$ ed. Edinburg: Churchill Livingstone, 1999.
8. Hoffman, A. S. "Hydrogels for Biomedical Applications." *Advanced Drug Delivery Reviews* 54.1 (2002): 3-12.
9. Park, H. N., and K. Park. "Hydrogels in Bioapplications." *Hydrogels and Biodegradable Polymers for Bioapplications*. Eds. R. M. Ottenbrite, S. J. Huang, and Kinam Park. Washington, D.C.: ACS Symposium Series 627, 1994.2-10.
10. Rosiak, J. M., and F. Yoshii. "Hydrogels and Their Mechanical Applications." *Nuclear Instruments and Methods in Physics Research* B 151.1-4 (1999): 56-64.
11. Gordon, M. J. "Controlling the Mechanical Properties of PVA Hydrogels For Biomedical Applications." Diss. Western Ontario U., 1999.
12. Hassan, C. M., and N. A. Peppas. "Structure and Applications of Poly(vinyl alcohol) Hydrogels Produced by Conventional Crosslinking or by Freezing/Thawing Methods." *Advances in Polymer Science* 153 (2000): 37-65.
13. Lozinsky, V. I., and F. M. Plieva. "Poly(vinyl alcohol) Cryogels Employed as Matrices for Cell Immobilization. 3. Overview of Recent Research and Developments." *Enzyme and Microbial Technology* 23.3-4 (1998): 227-42.
14. Ratner, B. D., et al., eds. *Biomaterials Science: An Introduction to Materials in Medicine*. San Diego: Academic Press, 1996.
15. Yannas, I. V., E. Lee, D. P. Orgill, "Synthesis and Characterization of a Model Extracellular Matrix that Induces Partial Regeneration of Adult Mammalian Skin." *Proc. Nati. Acad. Sci.* 86 (1989): 933-7.
16. Migliaresi, C., L. Nicodemo, and L. Nicolais. "Hydrogels for Artificial Tendons." *Hydrogels in Medicine and Pharmacy*. Ed. N. A. Peppas. Vol. 3. Boca Raton, Fla.: CRC Press, 1987.83-94.
17. Hui, A. J. "Hydrogel-Based Artificial Heart Valve Stent Material." Diss. Western Ontario U., 1998.
18. Sefton, M. V. "Heparinized Hydrogels." *Hydrogels in Medicine and Pharmacy*. Ed. N. A. Peppas. Vol. 3. Boca Raton, Fla.: CRC Press, 1987.17-52.
19. Korsmeyer, R. W., et al. "Mechanisms of Potassium Chloride Release from Compressed, Hydrophilic, Polymeric Matrices; Effect of Entrapped Air" *Journal of Pharmaceutical Science* 72 (1983): 1189-91.

20. Peppas, N. A. "Other Biomedical Applications of Hydrogels." *Hydrogels in Medicine and Pharmacy*. Ed. N. A. Peppas. Vol. 3. Boca Raton, Fla.: CRC Press, 1987.177-86.
21. Tighe, B. J. "Hydrogels as Contact Lens Materials." *Hydrogels in Medicine and Pharmacy*. Ed. N. A. Peppas. Vol. 3. Boca Raton, Fla.: CRC Press, 1987.53-82.
22. Peppas, N. A., and C. M. Hassan. "Structure and Applications of PVA Hydrogels Produced by Freezing/Thawing Methods." *Advances in Polymer Science* 8 (2000): 37-41.
23. Cascone, M. G., et al. "Evaluation of Poly(vinyl alcohol) Hydrogels as a Component of Hybrid Artificial Tissues." *Journal of Materials in Science: Materials in Medicine* 6 (1995): 71-5.
24. Ku, D. N., L. G. Braddon, and D. M. Wootton. *Poly(vinyl alcohol) Cryogel* U.S. Pat. No. 5,981,826 (1999).
25. Mori, Y., H. Tokura, and M. Yoshikawa. "Properties of Hydrogels Synthesized by Freezing and Thawing Aqueous Polyvinyl Alcohol Solutions and their Applications." *Journal of Materials Science* 32 (1997): 491-6.
26. Stauffer, S. R., and N. A. Peppas. "Poly(vinyl alcohol) Hydrogels Prepared by Freezing-Thawing Cyclic Processing." *Polymer* 33.18 (1992): 3932-5.
27. Trieu, H., and S. Qutubuddin. "Poly(vinyl alcohol) Hydrogels: 2. Effects of Processing Parameters on Structure and Properties." *Polymer* 36.13 (1995): 2531-9.
28. Hassan, C. M., and N. A. Peppas. "Structure and Morphology of Freeze/Thawed PVA Hydrogels." *Macromolecules* 33 (2000): 2472-2479.
29. Peppas, N. A., and S. R. Stauffer. "Reinforced Uncrosslinked Poly(vinyl alcohol) Gels Produced by Cyclic Freezing-Thawing Processes: A Short Review." *Journal of Controlled Release* 16 (1991): 305-10.
30. Chu, K. C., and B. K. Rutt. "Polyvinyl Alcohol Cryogel: An Ideal Phantom Material for MR Studies of Arterial Flow and Elasticity." *Magnetic Resonance in Medicine* 37 (1997): 314-9.
31. Joseph, G. A. "Studies of Bacterial Cellulose Production in Agitated Culture." Diss. Western Ontario U., 2001.
32. Klemm, D., et al. "Bacterial Synthesized Cellulose—Artificial Blood Vessel for Microsurgery." *Progress in Polymer Science* 26.9 (2001): 1561-603.
33. Eichhorn, S. J., et al. "Review Current International Research into Cellulosic Fibres and Composites." *Journal of Materials Science* 36.9 (2001): 2107-31.
34. Askeland, D. R. *The Science and Engineering of Materials*. 3$^{rd}$ ed. London: Chapman & Hall, 1996.
35. Uryu, M., and K. Tokura. Composite Polymer Materials and Process for Producing the Same U.S. Pat. No. 6,274,652 (2001).
36. Wan, W. K., et al. "Optimizing the Tensile Properties of Polyvinyl Alcohol Hydrogel for the Construction of a Bioprosthetic Heart Valve Stent." *Journal of Biomedical Materials Research* (Applied Biomaterials) 63 (2002): 854-861.

Therefore what is claimed is:

1. A hydrogel/cellulose composite material, comprising:
a hydrogel material present in an amount from 5% by weight to 15% by weight, and
cellulose present in a range from 0.05% by weight to 0.5% by weight, and
a remainder being a solvent, the cellulose including fibers having nanometer scale cross sectional dimensions;
wherein the hydrogel material is selected from the group consisting of polyvinyl alcohol (PVA), poly(vinyl pyrrolidone) (PVP), poly(ethylene glycol) (PEG), poly(hydroxyethyl methacrylate) (PHEMA) and polyacrylamide;
wherein the cellulose is microbially-produced cellulose; and
wherein the solvent is a hydroxylic solvent or an aprotic solvent capable of forming effective hydrogen bonding to dissolve the hydrogel material.

2. The composite material according to claim 1 wherein the solvent is water.

3. The composite material according to claim 2 wherein said cellulose having nanometer scale cross sectional dimensions is produced using a microbial fermentation process using one of a cellulose-producing bacterium and a cellulose-producing fungus.

4. The composite material according to claim 3 wherein the bacterium is from a genus of one of *Acetobacter, Pseudomonas, Achromobacter, Alcaligene, Aerobacter* and *Azotobacter*.

5. The composite material according to claim 3 wherein the bacterium is *Acetobacter xylinum* (ATCC#700178).

6. The composite material according to claim 5 wherein the hydrogel material is polyvinyl alcohol (PVA).

7. The composite material according to claim 6 wherein the polyvinyl alcohol (PVA) has a molecular weight in a range from about 100,000 to about 200,000.

8. The composite material according to claim 6 formed into a pre-selected shape for a medical application.

9. The composite material according to claim 8 wherein the pre-selected shape is selected from the group consisting of substantially planar sheets for wound dressings, dental implants, vascular grafts, catheter covering dressing, dialysis membranes, coatings for cardiovascular stents, coatings for cranial stents, and membranes for tissue guided regeneration.

10. The composite material according to claim 8 further including an effective bioactive agent contained therein which is released in a controlled manner from the composite material.

11. The composite material according to claim 3 wherein the fungus is from a genus of one of *Chaetomium, Saccharomyces, Candida, Pichia* and *Fusarium*.

12. The composite material according to claim 3 wherein said hydrogel material is polyvinyl alcohol (PVA).

13. A hydrogel/cellulose composite material, comprising: a hydrogel material including polyvinyl alcohol (PVA) present in an amount from 5% by weight to 15% by weight, cellulose present in a range from 0.05% by weight to 0.5% by weight and a remainder being water, the cellulose including fibers having nanometer scale cross sectional dimensions produced using a microbial fermentation process using a bacterium *Acetobacter xylinum*.

14. The composite material according to claim 13 wherein said polyvinyl alcohol (PVA) has a molecular weight in a range from about 100,000 to about 200,000.

15. The composite material according to claim 13 formed into a pre-selected shape for a medical application.

16. The composite material according to claim 15 wherein the pre-selected shape is selected from the group consisting of substantially planar sheets for wound dressings, dental implants, vascular grafts, catheter covering dressing, dialysis membranes, coatings for cardiovascular stents, coatings for cranial stents, and membranes for tissue guided regeneration.

17. The composite material according to claim 15 further including a selected bioactive agent contained therein which is released in a controlled manner from the composite material.

18. A hydrogel/cellulose composite material, comprising:
a hydrogel material present in an amount from 5% by weight to 15% by weight, and
cellulose present in a range from 0.05% by weight to 0.5% by weight, and
a remainder being a solvent, the cellulose including fibers having nanometer scale cross sectional dimensions;
wherein said composite is provided by mixing the hydrogel material with an aqueous suspension of said cellulose and subsequently physically crosslinking said hydrogel material to obtain said hydrogel/cellulose composite;
wherein the hydrogel material is selected from the group consisting of polyvinyl alcohol (PVA), poly(vinyl pyrrolidone) (PVP), poly(ethylene glycol) (PEG), poly(hydroxyethyl methacrylate) (PHEMA) and polyacrylamide;
wherein the cellulose is microbially-produced cellulose; and
wherein the solvent is a hydroxylic solvent or an aprotic solvent capable of forming effective hydrogen bonding to dissolve the hydrogel material.

19. A hydrogel/cellulose composite material, comprising:
a hydrogel material present in an amount from 5% by weight to 15% by weight, and
cellulose present in a range from 0.05% by weight to 0.5% by weight, and
a remainder being a solvent, the cellulose including fibers having nanometer scale cross sectional dimensions;
wherein an elastic modulus of said composite exceeds an elastic modulus of a material obtained by crosslinking said hydrogel in said solvent in absence of said cellulose;
wherein the hydrogel material is selected from the group consisting of polyvinyl alcohol (PVA), poly(vinyl pyrrolidone) (PVP), poly(ethylene glycol) (PEG), poly(hydroxyethyl methacrylate) (PHEMA) and polyacrylamide;
wherein the cellulose is microbially-produced cellulose; and
wherein the solvent is a hydroxylic solvent or an aprotic solvent capable of forming effective hydrogen bonding to dissolve the hydrogel material.

* * * * *